(12) United States Patent
Allegretti et al.

(10) Patent No.: US 8,026,367 B2
(45) Date of Patent: Sep. 27, 2011

(54) (R)-ARYLALKYLAMINO DERIVATIVES AND PHARMACEUTICAL COMPOSITIONS CONTAINING THEM

(75) Inventors: Marcello Allegretti, L'aquila (IT); Alessio Moriconi, L'aquila (IT); Andrea Aramini, L'aquila (IT); Maria Candida Cesta, L'aquila (IT); Andrea Beccari, L'aquila (IT); Riccardo Bertini, L'aquila (IT)

(73) Assignee: Dompe PHA.R.MA S.p.A., L'aquila (IT)

( * ) Notice: Subject to any disclaimer, the term of this patent is extended or adjusted under 35 U.S.C. 154(b) by 4 days.

(21) Appl. No.: 12/094,837

(22) PCT Filed: Nov. 24, 2006

(86) PCT No.: PCT/EP2006/068867
§ 371 (c)(1),
(2), (4) Date: Oct. 21, 2008

(87) PCT Pub. No.: WO2007/060215
PCT Pub. Date: May 31, 2007

(65) Prior Publication Data
US 2009/0124664 A1    May 14, 2009

(30) Foreign Application Priority Data
Nov. 24, 2005 (EP) .................................. 05111257

(51) Int. Cl.
*C07D 417/00* (2006.01)
*A01N 43/40* (2006.01)

(52) U.S. Cl. ........................ 546/270.7; 514/345; 514/357

(58) Field of Classification Search ................ 546/270.7; 514/357, 345
See application file for complete search history.

(56) References Cited

U.S. PATENT DOCUMENTS

| | | |
|---|---|---|
| 6,337,399 B1 | 1/2002 | Yamada et al. |
| 2005/0084506 A1 | 4/2005 | Tachdjian et al. |

FOREIGN PATENT DOCUMENTS

| | | |
|---|---|---|
| EP | 857725 A1 | 8/1998 |
| WO | WO 00/24710 | 5/2000 |
| WO | WO 02/068377 | 9/2002 |
| WO | WO 2005/090295 | 9/2005 |

OTHER PUBLICATIONS

Hcaplus 1994:323561, "Preparation of branched 2-(alkylamino)thiazole derivatives and their pharmaceutical compositions as CRF modulators", Courtemanche et. al., Dec. 29, 1993.*
Hcaplus 1998:561306, "Preparation of N-(pyridinylmethyl)-heterocyclylideneamine compounds as nicotinic acetylcholine receptor binding agents", Dorff et. al., Aug. 12, 1998.*
Allegretti, M. et al., Curr. Med. Chem., 2005, vol. 12, 217-236.*
Kim, G. et al., Neurosurgery, vol. 63, 2008, pp. 122-126.*
Al-Sehemi et al., "Kinetic Resolution of Amines with Enantiopure 3-N,N-diacylaminoquinazolin-4(3H)-ones," J. Chem. Soc., Perkin Trans. 1:257-274, 2002.
Beccalli et al., "Diastereoselective Synthesis of Enantiopure (αR)-2-methyl-4-(α-phenylethyl)-1,2,3,4-tetrahydro-benzo[e][1,4]diazepin-5-ones," Tetrahedron: Asymmetry 15:687-692, 2004.
Bucher et al., "Optisch Aktive 3-Amino-2H-azirine als Bausteine für Enantiomerenreine α, α-disubstituierte α-Aminosäuren: Synthese von Isovalin-Synthonen und Einbau in ein Trichotoxin-A-50-Segment," Helvetica Chinnica Acta 79:1903-1915, 1996.
Burns et al., "Chiral Phosphinamides: New Catalysts for the Asymmetric Reduction of Ketones by Borane," J. Chem. Soc., Perkin Trans. 1:1027-1038, 1998.
Chapela et al., "The Use of (R)-(+)-α-methylbenzylamine and (S)-(-)-α-methylbenzylamine as Chiral Moieties to Obtain Monomers for Second Harmonic Generation Crystals," J. Mol. Struct. 648:115-124, 2003.
Duhamel et al., "Déracémisation par Protonation Énantiosélective. Application à un α-aminoacide, la Phénylglycine," Bulletin De La Société Chimique De France 3-4:II-75-II-83, 1982.
Jennings et al., "Cyclobutane Carboxamide Inhibitors of Fungal Melanin: Biosynthesis and Their Evaluation as Fungicides," Bioorg. Med. Chem. 8:897-907, 2000.
Jursic et al., "Enantiomer Discrimination Arising from Solute-Solute Interactions in Partially Resolved Chloroform Solutions of Chiral Carboxamides," J. Org. Chem. 57:7172-7174, 1992.
Nerdel et al., "Darstellung und Rotationsdispersionen Optisch Aktiver α-Phenyl-Äthylamin-Derivate," Aus dem Organisch-Chemischen Institut der Technischen Universität Berlin, pp. 42-50, 1959. Ranogajec et al., "Enantiomer Separation and Molecular Recognition with New Chiral Stationary Phases on 4-Chloro-3,5-dinitrobenzoic Acid Amides of α,β-Aminoalcohols and α-Arylethylamines," J. Liq. Chromatog. Relat. Technol. 26:63-83, 2003.
Communication Relating to the Results of the Partial International Search from International Application No. PCT/EP2006/068867, enclosed with Invitation to Pay Additional Fees mailed Apr. 16, 2007.

(Continued)

*Primary Examiner* — Janet Andres
*Assistant Examiner* — Heidi Reese
(74) *Attorney, Agent, or Firm* — Clark & Elbing LLP

(57) ABSTRACT

The present invention relates to selected (R)-arylalkylamino derivatives of formula (I), in which R, R1 and Ar are as defined in the claims. These compounds show a surprising potent inhibitory effect on C5a induced human PMN chemotaxis. The compounds of the invention absolutely lack of CXCL8 inhibitory activity. Said compounds are useful in the treatment of pathologies depending on the chemotactic activation of neutrophils and monocytes induced by the fraction C5a of the complement. In particular, the compounds of the invention are useful in the treatment of sepsis, psoriasis, rheumatoid arthritis, ulcerative colitis, acute respiratory distress syndrome, idiopathic fibrosis, glomerulonephritis and in the prevention and treatment of injury caused by ischemia and reperfusion.

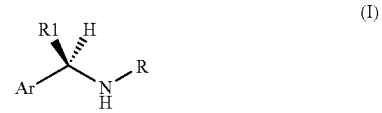

(I)

8 Claims, No Drawings

OTHER PUBLICATIONS

Bernstein et al., "The Common Basis of Intramolecular Rearrangements. V.[1] Inversion of Configuration in Semipinacolic Deamination. The Configurational Relationship between (+)-Alanine and (+)-Methylphenylacetic Acid," J. Am. Chem. Soc. 61:1324-1326, 1939.

Campbell et al., "Retention of Asymmetry During the Beckmann, Lossen, and Curtius Changes," J. Chem. Soc. 25-27, 1946.

Finke et al., "Orally Active β-Lactam Inhibitors of Human Leukocyte Elastase. 3.[1] Stereospecific Synthesis and Structure-Activity Relationships for 3,3-Dialkylazetidin-2-Ones," J. Med. Chem. 38:2449-2462, 1995.

Kenyon et al., "Retention of Asymmetry During the Curtius and the Beckmann Change," J. Chem. Soc. 263-267, 1941.

International Search Report from International Application No. PCT/EP2006/068867, search completed Aug. 8, 2007; International Search Report mailed Aug. 20, 2007.

\* cited by examiner

(R)-ARYLALKYLAMINO DERIVATIVES AND PHARMACEUTICAL COMPOSITIONS CONTAINING THEM

CROSS-REFERENCE TO RELATED APPLICATIONS

This application claims priority under 35 U.S.C. §371 from international application PCT/EP06/068867, filed Nov. 24, 2006, which claims priority from European Patent Application 05111257.1, filed Nov. 24, 2005.

INTRODUCTION AND BACKGROUND OF THE INVENTION

The present invention relates to novel compounds useful in the inhibition of the chemotactic activation induced by the fraction C5a of complement. Said compounds are useful in the treatment of pathologies depending on the chemotactic activation of neutrophils and monocytes induced by the fraction C5a of the complement. In particular, the compounds of the invention are useful in the treatment of sepsis, psoriasis, rheumatoid arthritis, ulcerative colitis, acute respiratory distress syndrome, idiopathic fibrosis, glomerulonephritis and in the prevention of injury caused by ischemia and reperfusion. In response to immunologic and infective events, activation of the complement system mediates amplification of inflammatory response both via direct membrane action and via release of a series of peptide fragments, generally known as anaphylatoxins, generated by enzymatic cleavage of the C3, C4 and C5 complement fractions. These peptides include C3a and C4a, both of 77 aminoacids; in turn, C5 convertase cleaves the C5 complement fraction to give the glycoprotein C5a of 74 aminoacids.

The C5a peptide fragment of the complement has been defined as the "complete" pro-inflammatory mediator due to its chemotactic and inflammatory activity. In fact, other inflammatory mediators such as selected cytokines (IL-8, MCP-1 and RANTES, for example) are highly selective towards self-attracted cells, while others such as histamine and bradykinin are only weak chemotactic agents.

Convincing evidences support the involvement of C5a, in vivo, in several pathological conditions including ischemia/reperfusion, autoimmune dermatitis, membrane-proliferative idiopathic glomerulonephritis, airway irresponsiveness and chronic inflammatory diseases, ARDS and CODP, Alzheimer's disease, juvenile rheumatoid arthritis (N. P. Gerard, Ann. Rev. Immunol., 12, 755, 1994).

In view of the neuro-inflammatory potential of C5a/C5a-desArg generated by both local complement production and amyloid activation joined with astrocyte and microglia chemotaxis and activation directly induced by C5a, complement inhibitors have been proposed for the treatment of neurological diseases such as Alzheimer's disease (McGeer & McGeer P. L., Drugs, 55, 738, 1998).

Furthermore, the control of the synthesis of complement fractions is considered a promising therapeutic target in the treatment of shock and in the prevention of rejection during organ transplant (multiple organ failure and hyperacute graft rejection) (Issekutz A. C. et al., Int. J. Immunopharmacol, 12, 1, 1990; Inagi R. et at., Immunol. Lett., 27, 49, 1991). More recently, inhibition of complement fractions has been reported to be involved in the prevention of native and transplanted kidney injuries taking account of complement involvement in the pathogenesis of both chronic interstitial and acute glomerular renal injuries. (Sheerin N. S. & Sacks S. H., Curr. Opinion Nephrol. Hypert., 7, 395, 1998).

Characteristic neutrophil accumulation occurs in acute and chronic pathologic conditions, for example in the highly inflamed and therapeutically recalcitrant areas of psoriatic lesions. Neutrophils are chemotactically attracted and activated by the synergistic action of chemokines, IL-8 and Gro-α released by the stimulated keratinocytes, and of the C5a/C5a-desArg fraction produced through the alternative complement pathway activation (T. Terui et al., Exp. Dermatol., 9, 1, 2000). We have recently described a novel class of "omega-aminoalkylamides of R-2-aryl-propionic acids" as inhibitors of the chemotaxis of polymorphonucleate and mononucleate cells" (WO 02/068377). The novel class includes compounds ranging from selective C5a inhibitors to dual C5a/IL-8 inhibitors.

Furthermore, quaternary ammonium salts of omega-aminoalkylamides of R-2-aryl-propionic acids have been reported as selective inhibitors of C5a induced neutrophils and monocytes chemotaxis (WO 03/029187).

DETAILED DESCRIPTION OF THE INVENTION

We have now surprisingly found novel (R)-arylalkylamino derivatives which exhibit a potent and selective inhibitory effect on C5a induced human PMN chemotaxis. The present invention relates to (R)-Arylalkylamino derivatives of formula (I):

wherein

R is selected from:

2-thiazolyl or 2-oxazolyl, unsubstituted or substituted by a group selected from methyl, tert-butyl or trifluoromethyl group;

$C(Ra)=N-W$ wherein W is linear or branched $C_1$-$C_4$ alkyl,

CORa, SORa, $SO_2Ra$, PORd, $PO_2Ra$, wherein

Ra is selected from $C_1$-$C_5$-alkyl, $C_3$-$C_6$-cycloalkyl, $C_2$-$C_5$-alkenyl, unsubstituted or substituted phenyl with a group selected from halogen, $C_1$-$C_4$-alkyl, $C_1$-$C_4$-alkoxy, halo-$C_1$-$C_4$-alkoxy, hydroxy, $C_1$-$C_4$-acyloxy, phenoxy, cyano, nitro, amino;

a heteroaryl group selected from pyridine, pyrimidine, pyrrole, thiophene, furane, indole, thiazole, oxazole, such heteroaryl being unsubstituted or substituted with a group selected from halogen, $C_1$-$C_4$-alkyl, $C_1$-$C_4$-alkoxy, halo-$C_1$-$C_4$-alkoxy, hydroxy, $C_1$-$C_4$-acyloxy, phenoxy, cyano, nitro, amino;

a α or β carboxyalkyl residue consisting of straight or branched $C_1$-$C_6$-alkyl, $C_3$-$C_6$-cycloalkyl, $C_2$-$C_6$-alkenyl, $C_1$-$C_6$-phenylalkyl, optionally substituted with a further carboxy (COOH) group;

an ω-aminoalkylamino group of formula II:

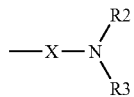

(II)

wherein
X represents:
   linear or branched $C_1$-$C_6$ alkylene, $C_4$-$C_6$ alkenylene, $C_4$-$C_6$ alkynylene, optionally substituted by a $CO_2R4$ group or by a CONHR5 group, wherein R4 represents hydrogen or a linear or branched $C_1$-$C_6$ alkyl group or a linear or branched $C_2$-$C_6$ alkenyl group, wherein R5 represents hydrogen, linear or branched $C_2$-$C_6$ alkyl or an OR4 group, R4 being defined as above;
   a $(CH_2)_m$—B—$(CH_2)_n$, group, optionally substituted by a $CO_2R4$ or CONHR5 group, as defined above, wherein B is an oxygen, or sulfur atom, or nitrogen atom optionally substituted by a $C_1$-$C_4$ alkyl group, m is zero or an integer from 2 to 3 and n is an integer from 2 to 3, or B is a CO, SO or CONH group, m is an integer from 1 to 3 and n is an integer from 2 to 3;
   or X together with the nitrogen atom to which it is bound and with the R2 group forms a nitrogen containing 3-7 membered heterocyclic, monocyclic or polycyclic ring, and R3 represents hydrogen, $C_1$-$C_4$ alkyl, $C_1$-$C_4$ acyl, unsubstituted or substituted phenyl with a group selected from halogen, $C_1$-$C_4$-alkyl, $C_1$-$C_4$-alkoxy, hydroxy, $C_1$-$C_4$-acyloxy, phenoxy, cyano, nitro, amino;
R2 and R3 are independently:
   hydrogen, linear or branched $C_1$-$C_6$ alkyl, optionally interrupted by an oxygen or sulfur atom, a $C_3$-$C_7$ cycloalkyl, $C_3$-$C_6$ alkenyl, $C_3$-$C_6$-alkynyl, aryl-$C_1$-$C_3$-alkyl, hydroxy-$C_2$-$C_3$-alkyl group; or R2 and R3 together with the N atom to which they are bound, form a 3-7 membered nitrogen heterocyclic ring of formula (III)

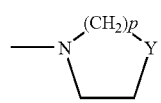

(III)

wherein
Y represents:
   a single bond, $CH_2$, O, S, or a N—R6 group, where R6 represents hydrogen, $C_1$-$C_4$ alkyl, $C_1$-$C_4$ acyl, unsubstituted or substituted phenyl with a group selected from halogen, $C_1$-$C_4$-alkyl, $C_1$-$C_4$-alkoxy, hydroxy, $C_1$-$C_4$-acyloxy, phenoxy, cyano, nitro, amino, and p represents an integer from 0 to 3;
   a residue of formula $SO_2R7$ wherein R7 is $C_1$-$C_6$-alkyl, $C_3$-$C_6$-cycloalkyl, $C_2$-$C_6$-alkenyl, aryl and heteroaryl;
R1 is linear or branched $C_1$-$C_5$ alkyl, $C_3$-$C_5$ cycloalkyl;
Ar is a phenyl group unsubstituted or substituted by one or more groups independently selected from halogen, $C_1$-$C_4$-alkyl, $C_1$-$C_4$-alkoxy, hydroxy, $C_1$-$C_4$-acyloxy, phenoxy, cyano, nitro, amino, $C_1$-$C_4$-acylamino, halo-$C_1$-$C_3$-alkyl, halo-$C_1$-$C_3$-alkoxy, benzoyl, heteroarylcarbonyl, heteroaryl, linear or branched $C_1$-$C_8$-alkanesulfonate, linear or branched $C_1$-$C_8$-alkanesulfonamides, linear or branched $C_1$-$C_8$ alkyl sulfonylmethyl;
   or Ar is a heteroaryl ring selected from pyridine, pyrrole, tiofene, furane, indole.
Preferred compounds according to the invention are those wherein:
R is
   2-thiazolyl, unsubstituted or substituted by a group selected from methyl or trifluoromethyl group;
   CORa, $SO_2Ra$, SORa;
wherein
Ra is selected from:
   $C_1$-$C_5$-alkyl, $C_3$-$C_5$-cycloalkyl;
   phenyl, 2-pyridyl, 2-thiazolyl, 2-furyl, 2-pyrrolyl, 2-thiofenyl, 2-indolyl groups;
   a carboxylalkyl group consisting of straight or branched $C_1$-$C_6$-alkyl, $C_1$-$C_6$-phenylalkyl group;
   an ω-alkylamino group of formula II,

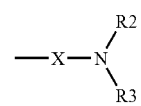

(II)

wherein
X represents:
   linear or branched $C_1$-$C_6$ alkylene, $C_4$-$C_6$ alkenylene, $C_4$-$C_6$ alkynylene;
   or X together with the nitrogen atom to which it is bound and with the R2 group forms a nitrogen containing 3-7 membered heterocyclic monocyclic ring and R3 represents hydrogen or $C_1$-$C_4$ alkyl;
R2 and R3 are independently hydrogen, linear or branched $C_1$-$C_6$ alkyl, $C_3$-$C_7$ cycloalkyl, $C_3$-$C_6$ alkenyl, $C_3$-$C_6$-alkynyl;
   or R2 and R3 together with the N atom to which they are bound, form a 4-6 membered nitrogen containing heterocyclic ring of formula (III)

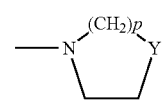

(III)

wherein Y represents $CH_2$, O, S, or a N—R7 group, where R7 represents hydrogen, $C_1$-$C_4$ alkyl, $C_1$-$C_4$ acyl, and p represents an integer from 0 to 2;
R1 is methyl;
Ar is selected from:
   3'-benzoylphenyl, 3'-(4-chloro-benzoyl)-phenyl, 3'-(4-methyl-benzoyl)-phenyl, 3'-acetyl-phenyl, 3'-propionyl-phenyl, 3'-isobutanoyl-phenyl, 4'-isobutyl-phenyl, 4'-trifluoromethanesulfonyloxy-phenyl, 4'-benzenesulfonyloxy-phenyl, 4'-trifluoromethanesulfonylamino-phenyl, 4'-benzenesulfonylamino-phenyl, 4'-benzenesulfonylmethyl-phenyl, 4'-acetoxyphenyl, 4'-propionyloxy-phenyl, 4'-benzoyloxy-phenyl, 4'-acetylamino-phenyl, 4'-propionylamino-phenyl, 4'-benzoylamino-phenyl;
   3'-(furan-2-carbonyl)-phenyl; 3'-(benzofuran-2-carbonyl)-phenyl; 3'-(thiophen-2-carbonyl)-phenyl; 3'-(pyridine-2-carbonyl)-phenyl, 3'-(thiazole-2-carbonyl)-phenyl, 3'-(oxazole-2-carbonyl)-phenyl; 3'-(2-furyl)-phenyl, 3'-(2-oxazolyl)-phenyl, 3'-(3-isoxazolyl)-phenyl, 3'-(2-benzoxazolyl)-phenyl, 3'-(3-benzoisoxazolyl)-phenyl, 3'-(2-thiazolyl)-phenyl, 3'-(2-pyridyl)-phenyl, 3'-(2-thiophenyl)-phenyl;

Examples of particularly preferred compounds of formula (I) are:
4-{(1R)-1-[(phenylsulfonyl)amino]ethyl}phenyl trifluoromethanesulfonate (1)
N-[(1R)-1-(3-benzoylphenyl)ethyl]benzenesulfonamide (2)
4-{(1R)-1-[(pyridine-3-ylsulfonyl)amino]ethyl}phenyl trifluoromethanesulfonate (3)
N-[(1R)-1-(3-benzoylphenyl)ethyl]methanesulfonamide (4)
N-[(1R)-1-[3-(2-furoyl)phenyl]ethyl}thiophene-2-sulfonamide (5)
N-[(1R)-1-[3-(2-furoyl)phenyl]ethyl}methanesulfonamide (6)
4-{(1R)-1-[(thien-2-ylsulfonyl)amino]ethyl}phenyl trifluoromethanesulfonate (7)
N-[(1R)-1-(3-benzoylphenyl)ethyl}thiophene-2-sulfonamide (8)
N-[(1R)-1-(3-benzoylphenyl)ethyl]-3-pyrrolidin-1-ylpropane-1-sulfonamide (9)
methyl 5-({[(1R)-1-(3-benzoylphenyl)ethyl]amino}sulfonyl)-2-furoate (10)
5-({[(1R)-1-(3-benzoylphenyl)ethyl]amino}sulfonyl)-2-furoic acid (11)
4-{(1R)-2-methyl-1-[(methylsulfonyl)amino]propyl}phenyl trifluoromethanesulfonate (12)
N-((1R)-1-{4-[1-methyl-1-(phenylsulfonyl)ethyl]phenyl}ethyl)methanesulfonamide (13)
4-[(1R)-1-(isobutyrylamino)ethyl]phenyl trifluoromethanesulfonate (14)
4{[(1R)-1-(pyridine-3-ylcarbonyl)amino]ethyl]}phenyl trifluoromethanesulfonate (15)
N-[(1R)-1-(3-benzoylphenyl)ethyl]benzamide (16)
N-[(1R)-1-(3-benzoylphenyl)ethyl]-2-furamide (17)
N-[(1R)-1-(3-benzoylphenyl)ethyl]cyclobutanecarboxamide (18)
N-[(1R)-1-(4-trifluoromethanesulfonyloxy)phenylethyl]-4-piperidin-1-ylbutanamide (19)
4-{(1R)-1-[(4-pyrrolidin-1-ylbutanoyl)amino]ethyl]}phenyl trifluoromethanesulfonate (20)
(3-{(1R)-1-[(4-trifluoramethyl-1,3-thiazol-2-yl)amino]ethyl]}phenyl) (phenyl)methanone (21).

Known methods for the preparation of formula (I) compounds have been used: the corresponding (R)-arylalkylamines of formula (IV)

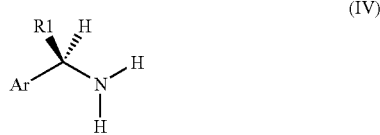

(IV)

wherein Ar and R1 are as above defined, have been prepared with a process comprising the steps of transforming the corresponding arylalkyl carboxylic acids in the acid azides, followed by the rearrangement of said azides in the corresponding isocyanates by Curtius reaction (March's Advanced Organic Chemistry, 5th Ed., 2001, Wiley Interscience, 1412-1413 and references therein), and final conversion of isocyanates into amines by acidic hydrolysis.

The carboxylic acids used as starting reagents are commercially available or prepared as described (Aureli L. et al. J. Med. Chem., 2005, 48, 2469). The reaction between the amines and commercially available alkyl or arylsulfonyl chlorides or acyl chlorides is performed according well known procedures.

The compounds of the invention of formula (I) were evaluated in vitro for their ability to inhibit chemotaxis of polymorphonucleate leukocytes (hereinafter referred to as PMNs) and monocytes induced by the fractions of the complement C5a and C5a-desArg. For this purpose, to isolate the PMNs from heparinized human blood, taken from healthy adult volunteers, mononucleates were removed by means of sedimentation on dextran (according to the procedure disclosed by W. J. Ming et al., J. Immunol., 138, 1469, 1987) and red blood cells by a hypotonic solution. The cell vitality was calculated by exclusion with Trypan blue, whilst the ratio of the circulating polymorphonucleates was estimated on the cytocentrifugate after staining with Diff Quick.

Human recombinant fractions C5a and C5a-desArg (Sigma) were used as stimulating agents in the chemotaxis experiments, giving practically identical results.

The lyophilized C5a was dissolved in a volume of HBSS containing 0.2% bovin serum albumin BSA so thus to obtain a stock solution having a concentration of $10^{-5}$ M to be diluted in HBSS to a concentration of $10^{-9}$ M, for the chemotaxis assays.

In the chemotaxis experiments, the PMNs were incubated with the compounds of the invention of formula (I) for 15' at 37° C. in an atmosphere containing 5% $CO_2$.

The chemotactic activity of the C5a was evaluated on human circulating polymorphonucleates (PMNs) resuspended in HBSS at a concentration of $1.5 \times 10^6$ PMNs per mL.

During the chemotaxis assay (according to W. Falket et al., J. Immunol. Methods, 33, 239, 1980) PVP-free filters with a porosity of 5 μm and microchambers suitable for replication were used.

The compounds of the invention in formula (I) were evaluated at a concentration ranging between $10^{-7}$ and $10^{-10}$ M; for this purpose they were added, at the same concentration, both to the lower pores and the upper pores of the microchamber. The wells in the lower part contain the solution of C5a or the simple carrier, those in the upper part contain the suspension of PMNs.

Inhibition of C5a-induced chemotactic activity by the individual compounds of the invention of formula (I) was evaluated by incubating the microchamber for the chemotaxis for 60 min at 37° C. in an atmosphere containing 5% $CO_2$.

Evaluation of the ability of the compounds of the invention of formula (I) to inhibit C5a-induced chemotaxis of human monocytes was carried out according to the method disclosed by Van Damme J. et al. (Eur. J. Immunol., 19, 2367, 1989). Inhibition of C5a-induced chemotactic activity by the individual compounds of the invention of formula (I) towards human monocytes was evaluated at a concentration ranging between $10^{-7}$ and $10^{-10}$ M by incubating the microchamber for the chemotaxis for 120 min. at 37° C. in an atmosphere containing 5% $CO_2$.

By way of example, the inhibition data of the chemotaxis of PMN (concentration range between $10^{-7}$ and $10^{-8}$ M) of some representative compounds of the invention are reported in Table 1.

The compounds of formula (I), were evaluated ex vivo in the blood in toto according to the procedure disclosed by Patrignani et al., in J. Pharmacol. Exper. Ther., 271, 1705, 1994. In almost all cases, the compounds of formula (I) do not interfere with the production of $PGE_2$ induced in murine macrophages by lipopolysaccharides stimulation (LPS, 1 μg/mL) at a concentration ranging between $10^{-5}$ and $10^{-7}$ M.

Inhibition of the production of PGE$_2$ is mostly at the limit of statistical significance, and generally below 15-20% of the basal value.

It is therefore a further object of the present invention the use of the compounds of the invention as medicaments.

In view of the experimental evidences discussed above and of the role performed by the complement cascade, and namely its fraction C5a, in the processes that involve the activation and the infiltration of neutrophils, the compounds of the invention are particularly useful in the treatment of diseases such as psoriasis (R. J. Nicholoff et al., Am. J. Pathol., 138, 129, 1991), bullous pemphigoid, sepsis, rheumatoid arthritis (M. Selz et al., J. Clin. Invest., 87, 463, 1981), intestinal chronic inflammatory pathologies such as ulcerative colitis (Y. R. Mahida et al., Clin. Sci., 82, 273, 1992), acute respiratory distress syndrome and idiopathic fibrosis (E. J. Miller, previously cited, and P. C. Carréet al., J. Clin. Invest., 88, 1882, 1991), cystic fibrosis, chronic obstructive pulmonary disease, glomerulonephritis (T. Wada et al., J. Exp. Med., 180, 1135, 1994) and in the prevention and the treatment of injury caused by ischemia and reperfusion.

To this purpose, the compounds of the invention of formula (I) are conveniently formulated in pharmaceutical compositions using conventional techniques and excipients such as those described in "Remington's Pharmaceutical Sciences Handbook" MACK Publishing, New York, 18th ed., 1990.

The compounds of the invention can be administered by intravenous injection, as a bolus, in dermatological preparations (creams, lotions, sprays and ointments), by inhalation as well as orally in the form of capsules, tablets, syrup, controlled-release formulations and the like.

The average daily dose depends on several factors such as the severity of the disease, the condition, age, sex and weight of the patient. The dose will vary generally from 1 to 1500 mg of compounds of formula (I) per day, optionally divided in multiple administrations.

The following examples illustrate the invention.

EXAMPLES

The alkyl and arylsulfonyl and the acyl chlorides used as reagents in the synthesis of compounds of formula (I) are known products, generally commercially available or they can be prepared according to methods described in the literature.

General Procedure for the Preparation of (1R)-1-Arylethanamines Intermediates

A. (2R)-2-[(4-trifluoromethanesulfonyloxy)phenyl] propanoyl azide (2R)-2-[(4-trifluoromethanesulfonyloxy)phenyl]propanoic acid[1] (8 g, 26.8 mmol) was dissolved in thionyl chloride (80 mL) and the resulting solution was refluxed until the complete disappearance of the starting material (3 h) as checked by FT-IR analysis. After cooling at room temperature, the solvent was evaporated under vacuum and toluene (15 mL) was added to the crude and evaporated twice to eliminate all the residues of thionyl chloride. To a cooled (0°-5° C.) solution of the residual yellow oil in CH$_2$Cl$_2$ (80 mL), tetrabutylammonium bromide (40 mg, 0.12 mmol) and a solution of sodium azide (2.7 g, 41.53 mmol) in H$_2$O (10 mL) were added and the resulting mixture was left stirring at room temperature overnight. An additional aliquot of sodium azide (1.7 g, 26.8 mmol) was added to complete the reaction. After 2 h the two phases were separated and the organic one was dried over Na$_2$SO$_4$, filtered and evaporated under vacuum to give an oily residue.

B. (1R)-1-[(4-trifluoromethanesulfonyloxy)phenyl] ethylamine hydrochloride

The reaction was performed according a well known procedure.[2] The crude acyl azide was dissolved in toluene (100 mL) and the resulting solution was refluxed until no more nitrogen was evolved. After cooling at 0°-5° C., 37% HCl (12 mL) was added and the resulting solution was heated under reflux overnight. After cooling at room temperature, H$_2$O was added (20 mL) and the two phases were separated. The aqueous one was basified with a saturated solution of NaHCO$_3$ to pH 8-9 and extracted with CH$_2$Cl$_2$ (3×50 mL). To the collected organic extracts a solution of acetyl chloride (1M) in EtOH (30 mL) was added by dripping and the resulting solution was left stirring for 1 h at room temperature. After solvents evaporation the solid was dried in oven at 40° C. under vacuum for 3 h to give pure (1R)-1-[(4-trifluoromethanesulfonyloxy)phenyl]ethylamine hydrochloride as white powder (6.69 g, 75% yield). m.p. 210-213° C.; $[\alpha]_D^{25}$ (c=0.5, CH$_3$OH): +6.5°; $^1$H-NMR (DMSO-d$_6$) δ 8.60 (bs, 3H, NH$_3^+$), 7.75 (d, 2H, J=7 Hz), 7.54 (d, 2H, J=7 Hz), 4.50 (m, 1H), 1.54 (d, 3H, J=7 Hz).

Following the procedure above described and starting from the appropriate carboxylic acids, the following amines were prepared:

(1R)-1-[(3-benzoyl)phenyl]ethylamine hydrochloride; white off powder; m.p. 200-203° C.; $[\alpha]_D^{25}$ (c=0.5, CH$_3$OH): +10°; $^1$H-NMR (CDCl$_3$) δ 9.15 (bs, 3H, NH$_3^+$), 8.12 (m, 2H), 7.95-7.80 (m, 3H), 7.70-7.55 (m, 4H), 4.60 (m, 1H), 1.65 (d, 3H, J=7 Hz).

(1R)-1-[(3-furoyl)phenyl]ethylamine hydrochloride; pale brown powder; m.p. 115-117° C.; $[\alpha]D^{25}$ (c=0.3, CH$_3$OH): +7°; $^1$H-NMR (CDCl$_3$) δ 8.90 (bs, 3H, NH$_3^+$), 8.12 (s, 1H), 7.90 (d, 1H, J=7 Hz), 7.80 (d, 1H, J=7 Hz), 7.70 (s, 1H), 7.48 (t, 1H, J=7 Hz), 7.35 (d, 1H, J=7 Hz), 6.60 (m, 1H), 4.55 (m, 1H), 1.80 (d, 3H, J=7 Hz).

Example 1

Synthesis of (1R)-1-arylethanesulfonamides (Compounds 1-8)

4-{(1R)-1-[(Phenylsulfonyl)amino]ethyl}phenyl trifluoromethanesulfonate (1)

To a solution of (1R)-1-[(4-trifluoromethanesulfonyloxy) phenyl]ethylamine hydrochloride (0.2 g, 0.65 mmol) in dry CH$_2$Cl$_2$ (3 mL), Na$_2$CO$_3$ (0.15 g, 1.44 mmol) and benzenesulfonyl chloride (92 µL, 0.72 mmol) were added and the resulting mixture was left stirring at room temperature overnight. The reaction was quenched by adding a NaH$_2$PO$_4$ buffer solution (pH 4.1-4.5) (5 mL) and EtOAc (10 mL). The two phases were separated and the organic one was dried over Na$_2$SO$_4$, filtered and evaporated under vacuum to give an oily residue. 1 was obtained pure after purification by flash chromatography (CHCl$_3$/CH$_3$OH 9:1) as a glassy solid (0.18 g, 68% yield). $[\alpha]_D^{25}$ (c=3, CH$_3$OH): +350; $^1$H-NMR (CDCl$_3$) δ 7.70 (d, 2H, J=7 Hz), 7.62 (m, 1H), 7.35 (d, 2H, J=7 Hz), 7.18 (d, 2H, J=7 Hz), 7.05 (d, 2H, J=7 Hz), 4.95 (bs, 1H, NH), 4.58 (q, 1H, J=7 Hz), 1.40 (d, 3H, J=7 Hz).

Following the procedure above described and starting from the described (1R)-1-arylethanamines and from the requested sulfonyl chlorides, the following 1-arylethanesulfonamides were prepared:

N-[(1R)-1-(3-Benzoylphenyl)ethyl]benzenesulfonamide (2); waxy solid; $[\alpha]_D^{25}$ (c=0.4, $CH_3OH$): +48.50; $^1$H-NMR ($CDCl_3$) δ 7.85 (m, 1H), 7.78 (d, 3H, J=7 Hz), 7.65 (m, 2H), 7.50-7.40 (m, 4H), 7.35-7.25 (m, 4H), 4.80 (bs, 1H, NH), 4.60 (q, 1H, J=7 Hz), 1.47 (d, 3H, J=7 Hz).

4-{(1R)-1-[(Pyridine-3-ylsulfonyl)amino]ethyl}phenyl trifluoromethanesulfonate (3); waxy solid; $[\alpha]_D^{25}$ (c=3, $CH_3OH$): +270; $^1$H-NMR ($CDCl_3$) δ 9.28 (s, 1H), 8.65 (d, 1H, J=7 Hz), 7.95 (d, 1H, J=7 Hz), 7.40 (m, 1H), 7.30 (d, 2H, J=7 Hz), 7.10 (d, 2H, J=7 Hz), 6.30 (bs, 1H, NH), 4.72 (q, 1H, J=7 Hz), 1.53 (d, 3H, J=7 Hz).

N-[(1R)-1-(3-Benzoylphenyl)ethyl]methanesulfonamide (4); yellow oil; $[\alpha]_D^{25}$ (c=1, $CH_3OH$): +45.50; $^1$H-NMR ($CDCl_3$) δ 7.92-7.80 (m, 3H), 7.75 (m, 1H), 7.65-7.58 (m, 2H), 7.52-7.45 (m, 3H), 4.80 (q, 1H, J=7 Hz), 4.65 (bs, 1H, NH), 2.80 (s, 3H), 1.72 (d, 3H, J=7 Hz).

N-[(1R)-1-[3-(2-Furoyl)phenyl]ethyl}thiophene-2-sulfonamide (5); white powder; m.p. 105-106° C.; $[\alpha]_D^{25}$ (c=1, $CH_3OH$): +720; $^1$H-NMR ($CDCl_3$) δ 7.85 (d, 1H, J=7 Hz), 7.70 (d, 2H, J=7 Hz), 7.50-7.38 (m, 3H), 7.20 (d, 1H, J=3 Hz), 6.95 (d, 1H, J=3 Hz), 6.65 (m, 1H), 4.90 (bs, 1H, NH), 4.68 (q, 1H, J=7 Hz), 1.55 (d, 3H, J=7 Hz).

N-[(1R)-1-[3-(2-Furoyl)phenyl]ethyl}methanesulfonamide (6); yellow oil; $[\alpha]_D^{25}$ (c=0.3, $CH_3OH$): +48°; $^1$H-NMR ($CDCl_3$) δ 8.02-7.90 (m, 2H), 7.75 (m, 1H), 7.60 (m, 1H), 7.42-7.35 (m, 1H), 7.28 (m, 1H), 6.65 (m, 1H), 4.80 (q, 1H, J=7 Hz), 4.65 (bs, 1H, NH), 2.75 (s, 3H), 1.65 (d, 3H, J=7 Hz).

4-{(1R)-1-[(Thien-2-ylsulfonyl)amino]ethyl}phenyl trifluoromethanesulfonate (7); colourless oil; $[\alpha]_D^{25}$ (c=0.6, $CH_3OH$): +31°; $^1$H-NMR ($CDCl_3$) δ 7.55 (d, 1H, J=7 Hz), 7.40 (d, 1H, J=7 Hz), 7.30 (d, 2H, J=7 Hz), 7.10 (d, 2H, J=7 Hz), 6.95 (m, 1H), 4.95 (bs, 1H, NH), 4.65 (q, 1H, J=7 Hz), 1.45 (d, 3H, J=7 Hz).

N-[(1R)-1-(3-Benzoylphenyl)ethyl}thiophene-2-sulfonamide (8); colourless oil; $[\alpha]_D^{25}$ (c=0.6, $CH_3OH$): +67°; $^1$H-NMR ($CDCl_3$) δ 7.80-7.70 (m, 2H), 7.68-7.55 (m, 3H), 7.50-7.42 (m, 5H), 7.35 (t, 1H, J=7 Hz), 6.90 (t, 1H, J=7 Hz), 5.15 (bs, 1H, NH), 4.65 (q, 1H, J=7 Hz), 1.50 (d, 3H, J=7 Hz).

Example 2

N-[(1R)-1-(3-benzoylphenyl)ethyl}-3-pyrrolidin-1-ylpropane-1-sulfonamide hydrochloride (9)

A. Preparation of N-[(1R)-1-(3-benzoylphenyl)ethyl]ethylenesulfonamide

To a solution of (1R)-1-[(3-benzoyl)phenyl]ethylamine hydrochloride (0.3 g, 1.14 mmol) in dry $CH_2Cl_2$ (10 mL), triethylamine (0.36 mL, 2.51 mmol) and 2-chloroethanesulfonyl chloride (0.14 mL, 1.37 mmol) were added, and the resulting mixture was left stirring at room temperature for 2 h. The reaction was quenched by adding $H_2O$ (10 mL). The two phases were separated and the organic one washed with 1N HCl (2×5 mL), dried over $Na_2SO_4$, filtered and evaporated under vacuum to give the intermediate N-[(1R)-1-(3-benzoylphenyl)ethyl]ethylenesulfonamide as an oily residue (0.3 g, 75% yield), pure enough for the next step. $^1$H-NMR ($CDCl_3$) δ 7.95-7-75 (m, 3H), 7.60 (d, 1H, J=7 Hz), 7.55-7.40 (m, 5H), 6.35 (m, 1H), 6.20 (d, 1H, J=15 Hz), 5.75 (d, 1H, J=8 Hz), 4.65 (m, 1H+NH), 1.60 (d, 3H, J=7 Hz).

B. Preparation of Compound 9

To a solution of N-[(1R)-1-(3-benzoylphenyl)ethyl]ethylenesulfonamide (0.28 g, 0.81 mmol) and triethylamine (0.11 mL, 0.81 mmol) in acetone (10 mL), pyrrolidine (68 μL, 0.81 mmol) was added by dripping. The resulting solution was left stirring at room temperature for 1 h and then refluxed for 3 h. After solvent evaporation the residue was diluted with 1N HCl (5 mL) and washed with $Et_2O$ (2×5 mL) and then with $CHCl_3$ (3×5 mL). The collected organic extracts in $CHCl_3$ were dried over $Na_2SO_4$, filtered and evaporated under vacuum to give a residue that, after purification by flash chromatography ($CHCl_3/CH_3OH$ 95:5), afforded the pure compound 9 as pale yellow oil (0.28 g, 82% yield). $[\alpha]_D^{25}$ (c=0.3, $CH_3OH$): +21°; $^1$H-NMR (DMSO-$d_6$) δ 10.40 (bs, 1H, NH$^+$), 8.18 (bs, 1H, NH), 7.80-7.70 (m, 2H), 7.68-7.55 (m, 3H), 7.50-7.42 (m, 4H), 4.65 (q, 1H, J=7 Hz), 3.60-3.40 (m, 6H), 2.95 (m, 2H), 1.97-1.78 (m, 4H), 1.45 (d, 3H, J=7 Hz).

Example 3

Methyl 5-({[(1R)-1-(3-benzoylphenyl)ethyl]amino}sulfonyl)-2-furoate (10)

A. Preparation of 5-(methoxycarbonyl)furan-2-sulfonate sodium salt

A solution of 2-furoyl chloride (1.5 g, 11.5 mmol) in $CH_3OH$ (20 mL) was left stirring at room temperature for 24 h. After solvent evaporation under vacuum, the crude residue was diluted with $CHCl_3$ (15 mL), washed with a saturated solution of $NaHCO_3$ (2×10 mL) and with $H_2O$ (10 mL), dried over $Na_2SO_4$ and evaporated under vacuum to give methyl 2-furoate as yellow oil (1.4 g, 97% yield). The ester was dissolved in fuming $H_2SO_4$ (0.2 mL) and left stirring overnight at room temperature. Crushed ice and cool $H_2O$ (5 mL) were carefully added, and then $BaCO_3$ was added (1.13 g, 5.75 mmol). The resulting suspension was heated to reflux and until the almost complete salt dissolution (3 h). After cooling at room temperature, barium sulfate was filtered off and the filtrate was evaporated under reduced pressure to give a crude which was diluted with 96% EtOH (30 mL) and refluxed for 2 h. The precipitate was filtered while hot and treated with a solution of $Na_2CO_3$ to pH 7.5-8.0; the formed precipitate (barium sulfate) was filtered off and the mother liquors evaporated under vacuum to give the intermediate 5-(methoxycarbonyl)furan-2-sulfonate sodium salt (1.325 g, 50% yield). $^1$H-NMR ($D_2O$) δ 7.05 (d, 1H, J=7 Hz), 6.80 (d, 1H, J=7 Hz), 3.82 (s, 3H). 5-(methoxycarbonyl)furan-2-sulfonate sodium salt (0.50 g, 2.19 mmol) was dissolved in $PCl_5$ (0.91 g, 4.38 mmol) and the mixture was left at 150° C. for 3 h, until the disappearance of the starting material (GC-Ms analysis). After cooling at room temperature, crushed ice and cool $H_2O$ were added and the aqueous phase was extracted with $CHCl_3$ (2×10 mL); the collected organic extracts were dried over $Na_2SO_4$, filtered and evaporated under vacuum to give the intermediate sulfonyl chloride (0.21 g, 0.95 mmol) used for the next step without any further purification.

B. Preparation of Compound 10

To a solution of (1R)-1-[(3-benzoyl)phenyl]ethylamine hydrochloride (0.22 g, 0.85 mmol) and triethylamine (0.24 mL, 1.8 mmol) in dry $CH_2Cl_2$ (2 mL), a solution of the sulfonyl chloride (0.21 g, 0.95 mmol) in dry $CH_2Cl_2$ (2 mL) was added by dripping. The resulting solution was left stirring at room temperature overnight. After solvent evaporation the crude oily residue was purified by flash chromatography ($CHCl_3$/n-hexane/$CH_3OH$ 80:20:1) and the pure compound 10 was isolated as white powder (0.14 g, 40% yield). $[\alpha]_D^{25}$ (c=0.2, CH$_2$Cl$_2$): −5°; $^1$H-NMR (CDCl$_3$) δ 7.75 (d, 2H, J=7 Hz), 7.60 (d, 3H, J=7 Hz), 7.50-7.35 (m, 3H), 7.30 (m, 1H), 6.95 (d, 1H, J=7 Hz), 6.80 (d, 1H, J=7 Hz), 5.20 (bs, 1H, NH), 4.70 (q, 1H, J=7 Hz), 3.85 (s, 3H), 1.55 (d, 3H, J=7 Hz).

Example 4

5-({[(1R)-1-(3-benzoylphenyl)ethyl] amino}sulfonyl)-2-furoic acid (11)

To a solution of methyl 5-({[(1R)-1-(3-benzoylphenyl) ethyl]amino}sulfonyl)-2-furoate (0.1 g, 0.24 mmol) in glacial AcOH (10 mL) few drops of 37% HCl were added and the resulting solution was refluxed for 12 h. After cooling at room temperature solvents were evaporated under vacuum, the residue was diluted with a saturated solution of NaHCO$_3$ (10 mL), washed with CHCl$_3$ (2×5 mL), acidified to pH 1 by 37% HCl and extracted again with CHCl$_3$ (2×5 mL). The collected organic extracts were dried over Na$_2$SO$_4$, filtered and evaporated under vacuum to give the pure compound 11 as a waxy solid (0.075 g, 78% yield). [α]$_D^{25}$ (c=0.5, CH$_2$Cl$_2$): −12°; $^1$H-NMR (CDCl$_3$) δ 7.75 (d, 2H, J=7 Hz), 7.60 (d, 3H, J=7 Hz), 7.50-7.35 (m, 3H), 7.30 (m, 1H), 7.05 (d, 1H, J=7 Hz), 6.85 (d, 1H, J=7 Hz), 5.75 (bs, 1H, NH), 4.78 (q, 1H, J=7 Hz), 4.50 (bs, 1H, COOH), 1.57 (d, 3H, J=7 Hz).

Example 5

4-{(1R)-2-Methyl-1-[(methylsulfonyl)amino] propyl}phenyl trifluoromethanesulfonate (12)

A. Preparation of (2R)-3-methyl-2-[4(trifluoromethylsllfonyloxy)phenyl]butanoic acid. To a solution of commercial 2-(4-chlorophenyl)-3-methylbutyric acid (1 g, 4.7 mmol) in CH$_3$OH (10 mL), few drops of conc. H$_2$SO$_4$ were added, and the resulting mixture was left stirring at room temperature overnight. After solvent evaporation under vacuum, CH$_2$Cl$_2$ (10 mL) and H$_2$O (10 mL) were added; the two phases were separated and the organic one dried over Na$_2$SO$_4$, filtered and evaporated under vacuum to give the intermediate methyl 2-(4-chlorophenyl)-3-methylbutanoate as an oily residue (quantitative yield). This intermediate was transformed in the related methyl 2-(4-hydroxyphenyl)-3-methylbutanoate according a known procedure[3]: a mixture of methyl 2-(4-chlorophenyl)-3-methylbutanoate (1.06 g, 4.7 mmol), 60% sodium hydride (0.56 g, 14.1 mmol) and H$_2$O (85 μL, 4.7 mmol) was heated to 45° C. while kept at argon atmosphere for 3 days ($^1$H-NMR analysis). The solvent was evaporated and the residue diluted with EtOAc and washed with 1N HCl (2×5 mL); the solvent was evaporated under vacuum and the crude residue was purified by flash chromatography (CHCl$_3$/CH$_3$OH 85:15) to give the pure intermediate as an oil (0.75 g, 77% yield). $^1$H-NMR (CDCl$_3$) δ 7.18 (d, 2H, J=7 Hz), 6.82 (d, 2H, J=7 Hz), 5.75 (bs, 1H, OH), 3.70 (s, 3H), 3.15 (d, 1H, J=14 Hz), 2.55 (m, 1H), 1.10 (d, 3H, J=7 Hz), 0.72 (d, 3H, J=7 Hz). The steps of insertion of the triflate group and the following hydrolysis were performed as described[1] and 3-methyl-2-[4-(trifluoromethylsulfonyloxy)phenyl]butanoic acid was obtained as a colourless oil (0.91 g, 78% yield calculated from the 4-hydroxy methyl ester derivative). The optical resolution was performed as described.[4] (2R)-3-methyl-2-[4-(trifluoromethylsulfonyloxy)phenyl]butanoic acid (0.32 g, 35% yield) was obtained as a white solid. [α]$_D^{25}$ (c=1, CH$_3$OH): −50°; $^1$H-NMR (CDCl$_3$) δ 7.55 (d, 2H, J=7 Hz), 7.25 (d, 2H, J=7 Hz), 3.15 (d, 1H, J=14 Hz), 2.55 (m, 1H), 1.10 (d, 3H, J=7 Hz), 0.72 (d, 3H, J=7 Hz).

B. The synthesis of compound 12 was performed as above described for compound 1. 4-{(1R)-2-methyl-1-[(methylsulfonyl)amino]propyl}phenyl trifluoro methane sulfonate was obtained as pale yellow oil. [α]$_D^{25}$ (c=0.5, CH$_3$OH): +15°; $^1$H-NMR (CDCl$_3$) δ 7.55 (d, 2H, J=7 Hz), 7.25 (d, 2H, J=7 Hz), 4.80 (m, 1H), 4.60 (bs, 1H, NH), 2.75 (s, 3H), 2.55 (m, 1H), 1.10 (d, 3H, J=7 Hz), 0.72 (d, 3H, J=7 Hz).

Example 6

N-((1R)-1-{4-[1-methyl-1-(phenylsulfonyl)ethyl] phenyl}ethyl)methanesulfonamide (13)

A. Preparation of N-((1R)-1-{4-[1-methyl-1-(phenylsulfonyl)ethyl]phenyl}propanoic acid 4-Iodophenylpropanenitrile was synthesised by known procedure[5] starting from the commercial 4-iodophenylacetonitrile. To a cooled (−78° C.) solution of 4-iodophenylpropanenitrile (0.26 g, 1 mmol) in dry THF (10 mL), isopropylmagnesium chloride (2M solution in THF) (1 mL, 2 mmol) and acetone (147 μL, 2 mmol) were added and the resulting mixture was left to raise to room temperature and stirring overnight. The reaction was quenched by adding a saturated solution of NH$_4$Cl (10 mL) and the aqueous phase was extracted with Et$_2$O (3×20 mL); the collected organic extracts, after drying over Na$_2$SO$_4$, were filtered and evaporated under vacuum to give a crude residue that, after purification by flash chromatography (n-hexane/EtOAc 9:1), afforded the intermediate 2-[4-(1-hydroxy-1-methylethyl) phenyl]propanenitrile (0.11 g, 60% yield) as colourless oil. $^1$H-NMR (CDCl$_3$) δ 7.45 (d, 2H, J=7 Hz), 7.20 (d, 2H, J=7 Hz), 3.90 (m, 1H), 2.05 (bs, 1H, OH), 1.70 (d, 3H, J=7 Hz), 1.55 (s, 6H). The following acid hydrolysis (AcOH/HCl/reflux/4 h) and the optical resolution[4] of the racemic acid afforded the (2R)-2-[4-(1-hydroxy-1-methylethyl)phenyl] propanoic acid as white solid. [α]$_D^{25}$ (c=1, CH$_3$OH): −12°; $^1$H-NMR (CDCl$_3$) δ 7.45 (d, 2H, J=7 Hz), 7.20 (d, 2H, J=7 Hz), 3.45 (m, 1H), 2.05 (bs, 1H, OH), 1.55 (s, 6H), 1.50 (d, 3H, J=7 Hz). A solution of the related methyl ester (0.22 g, 1 mmol) in CH$_2$Cl$_2$ (2 mL) was then reacted with thiophenol (0.12 mL, 1.2 mmol) according a described procedure[6] to obtain, after purification by flash chromatography and methyl ester hydrolysis, (2R)-2-{4-[1-methyl-1-(phenylthio)ethyl] phenyl}propanoic acid was obtained as pale yellow oil (0.18 g, 60% yield). $^1$H-NMR (CDCl$_3$) δ 7.45 (d, 2H, J=7 Hz), 7.25 (d, 2H, J=7 Hz), 7.20-7.05 (m, 5H), 3.45 (m, 1H), 1.50 (d, 3H, J=7 Hz), 1.25 (s, 6H). The oxidation of the sulfide to sulfone was accomplished according a published procedure.[7] To a cooled (0-5° C.) solution of the acid (0.15 g, 0.5 mmol) in CH$_3$OH (5 mL) magnesium bis(monoperoxyphtalate hexahydrate (MMPP) (0.5 g, 1 mmol) was added and the resulting mixture was left stirring for 4 h. After solvent evaporation under vacuum, the crude residue was purified by flash chromatography (n-hexane/EtOAc 8:2) to afford N-((1R)-1-{4-[1-methyl-1-(phenylsulfonyl)ethyl]phenyl}propanoic acid as a colourless oil (0.18 g, 55% yield). [α]$_D^{25}$ (c=1, CH$_3$OH): −32°; $^1$H-NMR (CDCl$_3$) δ 7.45 (d, 2H, J=7 Hz), 7.30-7.15 (m, 7H), 3.45 (m, 1H), 1.75 (s, 6H), 1.50 (d, 3H, J=7 Hz).

B. The synthesis of compound 13 was performed as above described for compound 1. N-((1R)-1-{4-[1-methyl-1-(phenylsulfonyl)ethyl]phenyl}ethyl)methane sulfonamide was obtained as colourless oil. [α]$_D^{25}$ (c=0.5, CH$_3$OH): +5°;

1H-NMR (CDCl$_3$) δ 7.45 (d, 2H, J=7 Hz), 7.30-7.15 (m, 7H), 4.65 (m, 1H), 4.40 (bs, 1H, NH), 2.62 (s, 3H), 1.75 (s, 6H), 1.48 (d, 3H, J=7 Hz).

Example 7

Preparation of (1R)-1-arylethylamides (Compounds 14-20)

4-[(1R)-1-(Isobutyrylamino)ethyl]phenyl trifluoromethanesulfonate (14) To a solution of (1R)-1-[(4-trifluoromethanesulfonyloxy)phenyl]ethylamine hydrochloride (0.2 g, 0.65 mmol) in pyridine (5 mL), isobutyryl chloride (75 μL, 0.72 mmol) was added and the resulting mixture was refluxed for 1 h. After cooling at room temperature, the solvent was evaporated under vacuum and the crude residue diluted with EtOAc (5 mL) and washed with 1N HCl (2×10 mL). The organic phase was dried over Na$_2$SO$_4$, filtered and evaporated under vacuum to give an oily residue. 14 was obtained pure after purification by flash chromatography (CHCl$_3$/CH$_3$OH 95:5) as a colourless oil (0.165 g, 75% yield). [α]$_D^{25}$ (c=0.5, CH$_3$OH): +10°; $^1$H-NMR (CDCl$_3$) δ 7.45 (d, 2H, J=7 Hz), 7.30 (d, 2H, J=7 Hz), 5.70 (bs, 1H, NH), 5.15 (q, 1H, J=7 Hz), 2.35 (m, 1H), 1.52 (d, 3H, J=7 Hz), 1.15 (d, 6H, J=7 Hz).
Following the procedure above described and starting from the described (1R)-1-arylethanamines and from the requested acyl chlorides, the following 1-arylethylamides were prepared:

4-{[(1R)-1-(Pyridine-3-ylcarbonyl)amino]ethyl]}phenyl trifluoro methane sulfonate (15); white powder; m.p. 120-122° C.; [α]$_D^{25}$ (c=1, CH$_3$OH): −1.5°; $^1$H-NMR (CDCl$_3$) δ 9.05 (s, 1H), 8.78 (d, 1H, J=7 Hz), 8.15 (d, 1H, J=7 Hz), 7.50 (d, 2H, J=7 Hz), 7.35 (m, 1H), 7.27 (d, 2H, J=7 Hz), 6.50 (bs, 1H, NH), 5.35 (q, 1H, J=7 Hz), 1.65 (d, 3H, J=7 Hz).

N-[(1R)-1-(3-Benzoylphenyl)ethyl]benzamide (16); colourless oil; [α]$_D^{25}$ (c=0.5, CH$_3$OH): +180; $^1$H-NMR (CDCl$_3$) δ 7.90 (m, 1H), 7.80-7.70 (m, 4H), 7.65-7.52 (m, 4H), 7.45-7.30 (m, 5H), 6.40 (bs, 1H, NH), 5.35 (q, 1H, J=7 Hz), 1.65 (d, 3H, J=7 Hz).

N-[(1R)-1-(3-Benzoylphenyl)ethyl]-2-furamide (17); pale yellow oil; [α]$_D^{25}$ (c=1.7, CH$_3$OH): −50.5°; $^1$H-NMR (CDCl$_3$) δ 7.90 (s, 1H), 7.78 (d, 2H, J=7 Hz), 7.70-7.55 (m, 3H), 7.45 (m, 4H), 7.14 (d, 1H, J=3 Hz), 6.58 (bs, 1H, NH), 6.50 (d, 1H, J=3 Hz), 5.35 (q, 1H, J=7 Hz), 1.68 (d, 3H, J=7 Hz).

N-[(1R)-1-(3-Benzoylphenyl)ethyl]cyclobutanecarboxamide (18); white solid; m.p. 90-93° C.; [α]$_D^{25}$ (c=0.3, CH$_3$OH): +91°; $^1$H-NMR (CDCl$_3$) δ 7.80-7.70 (m, 4H), 7.65 (m, 1H), 7.60-7.50 (m, 4H), 5.55 (bs, 1H, NH), 5.20 (q, 1H, J=7 Hz), 3.00 (m, 1H), 2.35-2.10 (m, 4H), 2.05-1.80 (m, 2H), 1.45 (d, 3H, J=7 Hz).

Example 9

Compounds 19-20

N-[(1R)-1-(4-trifluoromethanesulfonyloxy)phenylethyl]-4-piperidin-1-ylbutanamide (19)

A. Preparation of sodium 4-piperidin-1-ylbutanoate

To a solution of ethyl 4-chlorobutyrate (0.5 g, 3.32 mmol) in DMF (2 mL), piperidine (0.98 mL, 9.96 mmol), triethylamine (1.4 mL, 9.96 mmol) and a catalytic amount of KI were added and the resulting solution was refluxed overnight. After cooling at room temperature the solution was diluted with a saturated solution of NaHCO$_3$ (10 mL) and extracts with Et$_2$O (3×10 mL). The collected organic extracts were dried over Na$_2$SO$_4$, filtered and evaporated under vacuum to give the ethyl 4-piperidin-1-ylbutanoate as an oily residue (0.6 g, 3 mmol) pure enough for the next step. To a solution of the ester in dioxane (5 mL), few drops of 37% HCl were added and the solution was refluxed overnight. After cooling at room temperature the solvent was evaporated under vacuum and the residue was dried overnight in oven at 60° C. in vacuo. The crude 4-piperidin-1-ylbutanoic acid was dissolved in CH$_3$OH (4 mL) and NaHCO$_3$ (0.5 g, 6 mmol) was added. After stirring for 2 h, the precipitate was filtered off and the mother liquors concentrated to afford the intermediate sodium 4-piperidin-1-ylbutanoate (0.55 g, 2.84 mmol) as a colourless oil. $^1$H-NMR (DMSO-d$_6$) δ 3.35 (m, 2H), 2.80 (m, 2H), 2.70 (m, 2H), 2.15 (t, 2H, J=3 Hz), 1.95 (m, 2H), 1.75 (m, 6H).

B. Preparation of Compound 15

To a solution of sodium 4-piperidin-1-ylbutanoate (0.41 g, 2.13 mmol) in dry CH$_2$Cl$_2$ (10 mL), 1,1'-carbonyldiimidazole (0.34 g, 2.13 mmol) was added and the resulting solution was left stirring at room temperature for 1 h. Triethylamine (0.59 mL, 4.25 mmol) and (1R)-1-[(4-trifluoromethanesulfonyloxy)phenyl]ethylamine hydrochloride (0.65 g, 2.13 mmol) were added and the resulting solution was left stirring at room temperature overnight. A saturated solution of NaHCO$_3$ (10 mL) was added and the two phases separated. The organic one was washed with extracts with a saturated solution of NaHCO$_3$ (2×5 mL), dried over Na$_2$SO$_4$, filtered and evaporated under vacuum to give an oily residue. The crude was purified by flash chromatography (CHCl$_3$/CH$_3$OH/cyclohexane/NH$_4$OH 60:14:24:2) and the eluted free base, after treatment with an excess of acetyl chloride in EtOH (1.4 M), afforded N-[(1R)-1-(4-trifluoromethanesulfonyloxy)phenylethyl]-4-piperidin-1-ylbutanamide 15 in form of hydrochloride (0.734 g, 75% yield) as pale yellow oil. [α]$_D^{25}$ (c=0.3, CH$_3$OH): +51.5°; $^1$H-NMR (DMSO-d$_6$) δ 9.95 (bs, 1H, NH$^+$), 8.55 (bs, 1H, NH), 7.45 (q, 4H, J=7 Hz), 4.90 (q, 1H, J=7 Hz), 3.35 (m, 2H), 2.92 (m, 2H), 2.80 (m, 2H), 2.25 (t, 2H, J=3 Hz), 1.95 (m, 2H), 1.75 (m, 6H).

4-{(1R)-1-[(4-pyrrolidin-1-ylbutanoyl)amino]ethyl]}phenyl trifluoro methane sulfonate (20)

The synthesis of compound 20 was performed as above described for compound 19. 4-{(1R)-1-[(4-pyrrolidin-1-ylbutanoyl)amino]ethyl]}phenyl trifluoromethanesulfonate was obtained as colourless oil. [α]$_D^{25}$ (c=0.1, CH$_3$OH): +40°; $^1$H-NMR (CDCl$_3$) δ 7.60 (bs, 1H, NH), 7.40 (d, 2H, J=7 Hz), 7.25 (d, 2H, J=7 Hz), 5.15 (q, 1H, J=7 Hz), 2.55 (m, 6H), 2.35 (t, 2H, J=3 Hz), 1.85-1.70 (m, 6H), 1.45 (d, 3H, J=7 Hz).

Example 10

(3-{(1R)-1-[(4-trifluoromethyl-1,3-thiazol-2-yl)amino]ethyl]}phenyl) (phenyl)methanone (21)

To a solution of (1R)-1-[(3-benzoyl)phenyl]ethylamine hydrochloride (0.52 g, 2 mmol) in toluene (15 mL), conc. H$_2$SO$_4$ (3 mmol) and sodium thiocyanate (0.18 g, 2.2 mmol) were added and the resulting mixture was left stirring at room temperature for 30 min. The formation of a white precipitate was observed: then the mixture was refluxed for 4 h and left stirring at room temperature overnight. The organic phase was washed with H₂O (3×mL), dried over Na₂SO₄, filtered and evaporated under vacuum to give the N-[(1R)-1-(3-benzoylphenyl)ethyl]thiourea a dark red oil (0.53 g) pure enough (GC-Ms analysis) to be used without any further purification.

To a solution of thiourea (0.2 g, 0.7 mmol) in dry THF (10 mL) 3-bromo-1,1,1-trifluoroacetone (0.27 g, 1.4 mmol) and the resulting solution was left stirring at 40° C. overnight. After cooling at room temperature, the solution was evaporated under vacuum and the crude was diluted with EtOAc (20 mL) and a saturated solution of NaHCO₃ (15 mL); The two phases were separated and the organic one was washed with a saturated solution of NaCl, dried over Na₂SO₄, filtered and evaporated under vacuum to give a crude that, after purification by flash chromatography (eluent mixture n-hexane/EtOAc 9:1), afforded 21 (0.185 g, 70% yield) as colourless oil. $[\alpha]_D^{25}$ (c=0.1, CH₃OH): +44°; 1H-NMR (CDCl₃) δ 7.80-7.70 (m, 4H), 7.65 (m, 2H), 7.60-7.50 (m, 3H), 6.90 (s, 1H), 5.75 (bs, 1H, NH), 4.80 (q, 1H, J=7 Hz), 1.65 (d, 3H, J=7 Hz).

REFERENCES

1—Aureli L. et al. *J. Med. Chem.*, 2005, 48, 2469.
2—Banthorpe D. V. in Patai *The Chemistry of the Azido Group*; Wiley: NY, 1971, 397.
3—Widdowson K. L. et al., U.S. Pat. No. 6,608,077 (Aug. 19, 2003).
4—Akgun, H. et al., *Arzneimittelforschung*, 1996, 46, 891.
5—Kaltenbronn J. S. *J. Med. Chem.*, 1973, 16, 490.
6—Gauthier J. Y. et al., *Tetrahedron Lett.*, 1986, 27, 15.
7—(a) Arjona O. et al., *J. Org. Chem.*, 2001, 66, 2400. (b) Arjona O. et al., *Tetrahedron*, 2001, 57, 6751.

TABLE 1

Compounds active on PMNs C5a induced chemotaxis

| Ex. | Structure | Chemical Name | % inhibition C5a induced PMN migration |
|---|---|---|---|
| 1 | 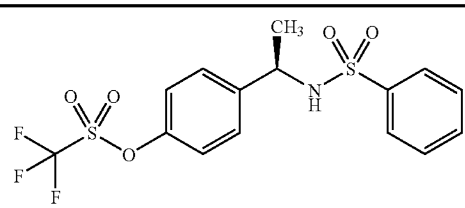 | 4-{(1R)-1-[(phenylsulfonyl)amino]ethyl}phenyl trifluoromethanesulfonate | 50 ± 1* |
| 2 | 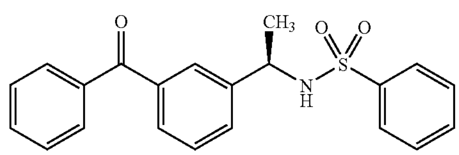 | N-[(1R)-1-(3-benzoylphenyl)ethyl]benzenesulfonamide | 59 ± 10 |
| 3 | 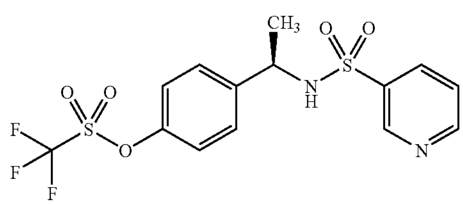 | 4-{(1R)-1-[(pyridine-3-ylsulfonyl)amino]ethyl}phenyl trifluoromethanesulfonate | 47 ± 7 |
| 4 | 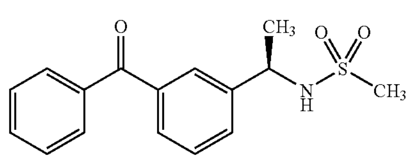 | N-[(1R)-1-(3-benzoylphenyl)ethyl]methanesulfonamide | 48 ± 8 |
| 5 | 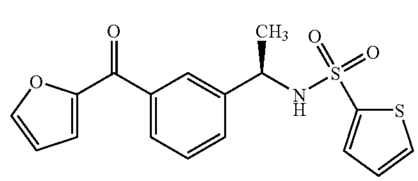 | N-[(1R)-1-[3-(2-furoyl)phenyl]ethyl}thiophene-2-sulfonamide | 60 ± 8 |
| 6 | 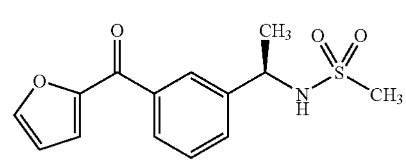 | N-[(1R)-1-[3-(2-furoyl)phenyl]ethyl}methanesulfonamide | 52 ± 7 |

TABLE 1-continued

Compounds active on PMNs C5a induced chemotaxis

| Ex. | Structure | Chemical Name | % inhibition C5a induced PMN migration |
|---|---|---|---|
| 7 | 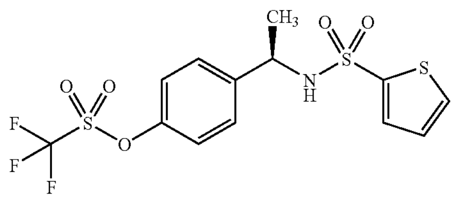 | 4-{(1R)-1-[(thien-2-ylsulfonyl)amino]ethyl}phenyl trifluoromethanesulfonate | 41 ± 8 |
| 8 | 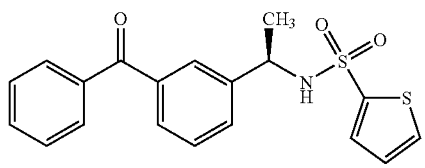 | N-[(1R)-1-(3-benzoylphenyl)ethyl}thiophene-2-sulfonamide | 55 ± 14 |
| 9 | 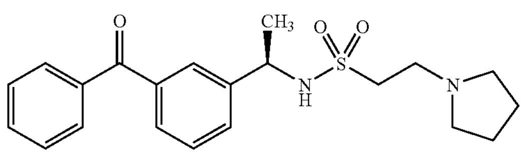 | N-[(1R)-1-(3-benzoylphenyl)ethyl}-3-pyrrolidin-1-ylpropane-1-sulfonamide | 38 ± 3 |
| 10 | 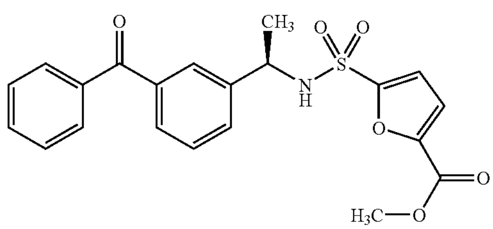 | methyl 5-({[(1R)-1-(3-benzoylphenyl)ethyl]amino}sulfonyl)-2-furoate | 72 ± 6 |
| 11 | 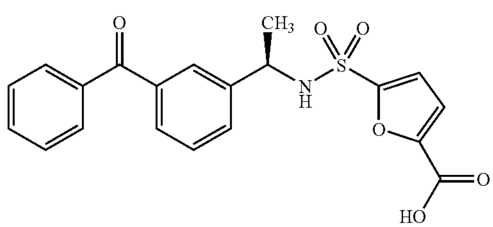 | 5-({[(1R)-1-(3-benzoylphenyl)ethyl]amino}sulfonyl)-2-furoic acid | 40 ± 4 |
| 12 | 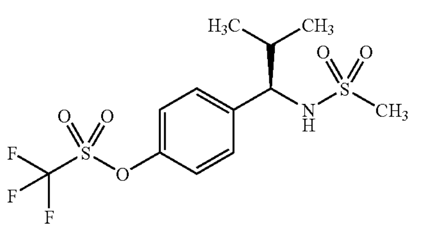 | 4-{(1R)-2-methyl-1-[(methylsulfonyl)amino]propyl}phenyl trifluoromethanesulfonate | 40 ± 5 |
| 13 | 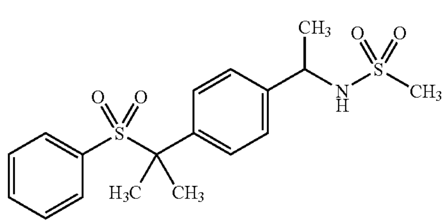 | N-((1R)-1-{4-[1-methyl-1-(phenylsulfonyl)ethyl]phenyl}ethyl) methanesulfonamide | 64 ± 8 |

TABLE 1-continued

Compounds active on PMNs C5a induced chemotaxis

| Ex. | Structure | Chemical Name | % inhibition C5a induced PMN migration |
|---|---|---|---|
| 14 | 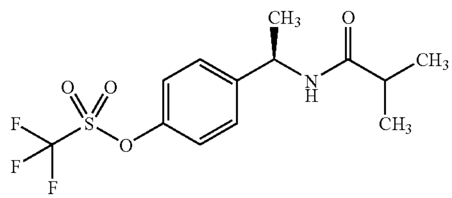 | 4-[(1R)-1-(isobutyrylamino)ethyl]phenyl trifluoromethanesulfonate | 60 ± 8 |
| 15 | 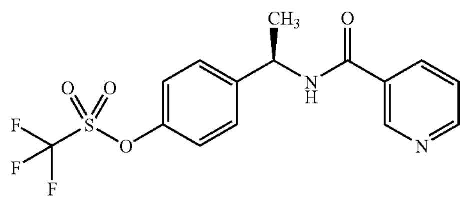 | 4-{[(1R)-1-(pyridine-3-ylcarbonyl)amino]ethyl]}phenyl trifluoromethanesulfonate | 46 ± 6 |
| 16 | 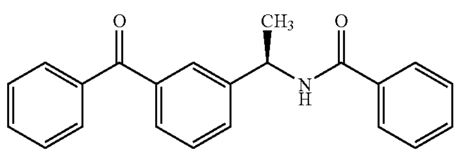 | N-[(1R)-1-(3-benzoylphenyl)ethyl]benzamide | 49 ± 5* |
| 17 | 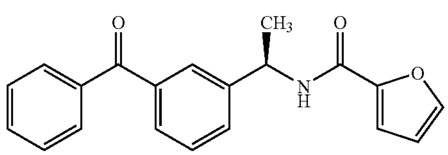 | N-[(1R)-1-(3-benzoylphenyl)ethyl]-2-furamide | 63 ± 10 |
| 18 | 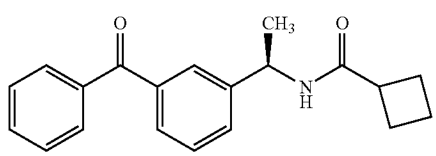 | N-[(1R)-1-(3-benzoylphenyl)ethyl]cyclobutanecarboxamide | 57 ± 4 |
| 19 | 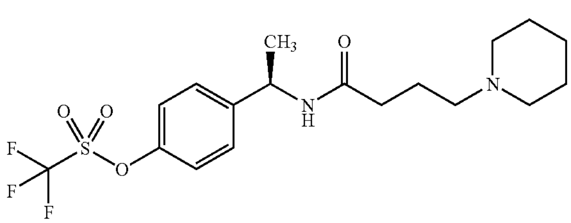 | N-[(1R)-1-(4-trifluoromethanesulfonyloxy)phenylethyl]-4-piperidin-1-ylbutanamide | 54 ± 17 |
| 20 | 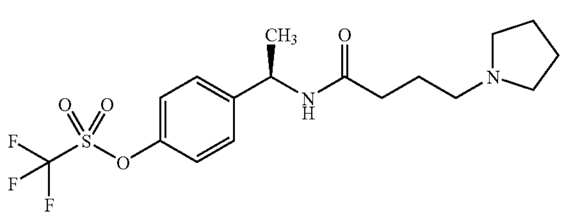 | 4-{(1R)-1-[(4-pyrrolidin-1-ylbutanoyl)amino]ethyl]}phenyl trifluoromethanesulfonate | 47 ± 1 |

TABLE 1-continued

Compounds active on PMNs C5a induced chemotaxis

| Ex. | Structure | Chemical Name | % inhibition C5a induced PMN migration |
|---|---|---|---|
| 21 | 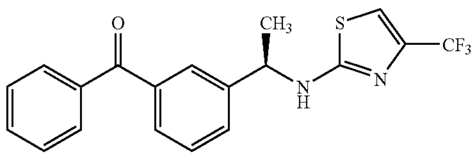 | (3-{(1R)-1-[(4-trifluoromethyl-1,3-thiazol-2-yl)amino]ethyl}phenyl)(phenyl)methanone | 42 ± 5 |

The invention claimed is:

1. (R)-Arylalkylamino derivatives of formula (I):

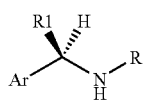

wherein

R is selected from:
  2-thiazolyl or 2-oxazolyl, unsubstituted or substituted by a methyl, tert-butyl or trifluoromethyl group;
  $C(Ra)=N-W$ wherein W is linear or branched $C_1$-$C_4$ alkyl, or
  CORa, SORa, or $SO_2Ra$,
wherein
Ra is selected from
  $C_1$-$C_5$-alkyl, $C_3$-$C_6$-cycloalkyl, $C_2$-$C_5$-alkenyl, or phenyl unsubstituted or substituted with a group selected from halogen, $C_1$-$C_4$-alkyl, $C_1$-$C_4$-alkoxy, halo-$C_1$-$C_4$-alkoxy, hydroxy, $C_1$-$C_4$-acyloxy, phenoxy, cyano, nitro, or amino;
  a heteroaryl group selected from pyridine, pyrimidine, pyrrole, thiophene, furan, indole, thiazole, or oxazole, such heteroaryl being unsubstituted or substituted with a group selected from halogen, $C_1$-$C_4$-alkyl, $C_1$-$C_4$-alkoxy, halo-$C_1$-$C_4$-alkoxy, hydroxy, $C_1$-$C_4$-acyloxy, phenoxy, cyano, nitro, or amino;
  an α or β carboxyalkyl residue of straight or branched $C_1$-$C_6$-alkyl, $C_3$-$C_6$-cycloalkyl, $C_2$-$C_6$-alkenyl, or $C_1$-$C_6$-phenylalkyl, optionally substituted with a further carboxy (COOH) group; or
  an ω-aminoalkylamino group of formula II:

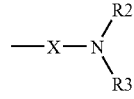

wherein
X represents:
  linear or branched $C_1$-$C_6$ alkylene, $C_4$-$C_6$ alkenylene, $C_4$-$C_6$ alkynylene, optionally substituted by a $CO_2R4$ group or by a CONHR5 group, wherein R4 represents hydrogen or a linear or branched $C_1$-$C_4$ alkyl group or a linear or branched $C_2$-$C_6$ alkenyl group, and wherein R5 represents hydrogen, linear or branched $C_2$-$C_6$ alkyl or an OR4 group, R4 being defined as above; or a $(CH_2)_m$—B—$(CH_2)_n$, group, optionally substituted by a $CO_2R4$ or CONHR5 group, as defined above, wherein B is an oxygen, sulfur, or nitrogen atom optionally substituted by a $C_1$-$C_4$ alkyl group, m is zero or an integer from 2 to 3 and n is an integer from 2 to 3, or B is a CO, SO, or CONH group, m is an integer from 1 to 3 and n is an integer from 2 to 3;

or X together with the nitrogen atom to which it is bound and with the R2 group forms a nitrogen containing 3-7 membered heterocyclic, monocyclic or polycyclic ring, and R3 represents hydrogen, $C_1$-$C_4$ alkyl, $C_1$-$C_4$ acyl, or phenyl unsubstituted or substituted with a group selected from halogen, $C_1$-$C_4$-alkyl, $C_1$-$C_4$-alkoxy, hydroxy, $C_1$-$C_4$-acyloxy, phenoxy, cyano, nitro, or amino;

R2 and R3 are independently:
  hydrogen, linear or branched $C_1$-$C_6$ alkyl, optionally interrupted by an oxygen or sulfur atom, $C_3$-$C_7$ cycloalkyl, $C_3$-$C_6$ alkenyl, $C_3$-$C_6$-alkynyl, aryl-$C_1$-$C_3$-alkyl, or hydroxy-$C_2$-$C_3$-alkyl group; or R2 and R3 together with the N atom to which they are bound, form a 3-7 membered nitrogen heterocyclic ring of formula (III)

$$-N\underset{}{\overset{(CH_2)p}{\diagup\diagdown}}Y$$ (III)

wherein
Y represents:
  a single bond, $CH_2$, O, S, or a N—R6 group, where R6 represents hydrogen, $C_1$-$C_4$ alkyl, $C_1$-$C_4$ acyl, or phenyl unsubstituted or substituted with a group selected from halogen, $C_1$-$C_4$-alkyl, $C_1$-$C_4$-alkoxy, hydroxy, $C_1$-$C_4$-acyloxy, phenoxy, cyano, nitro, or amino, and p represents an integer from 0 to 3; or
  a residue of formula $SO_2R7$ wherein R7 is $C_1$-$C_6$-alkyl, $C_3$-$C_6$-cycloalkyl, $C_2$-$C_6$-alkenyl, aryl or heteroaryl;

R1 is linear or branched $C_1$-$C_5$ alkyl, or $C_3$-$C_5$ cycloalkyl; and

Ar is 3'-benzoylphenyl, 3'-(4-chloro-benzoyl)-phenyl, 3'-(4-methyl-benzoyl)-phenyl, 3'-acetyl-phenyl, 3'-propionyl-phenyl, 3'-isobutanoyl-phenyl, 4'-trifluoromethanesulfonyloxy-phenyl, 4'-benzenesulfonyloxy-phenyl, 4'-trifluoromethanesulfonylamino-phenyl, 4'-benzenesulfonylamino-phenyl, 4'-benzenesulfonylmethyl-phenyl, 4'-acetoxyphenyl, 4'-propionyloxy-phenyl, 4'-benzoyloxy-phenyl, 4'-benzoylamino-phenyl, 3'-(furan-2-carbonyl)-phenyl, 3'-(benzofuran-2-carbonyl)-phenyl, 3'-(thiophene-2-carbonyl)-phenyl; 3'-(pyridine-2-carbonyl)-phenyl, 3'-(thiazole-2-carbonyl)-phenyl, 3'-(oxazole-2-carbonyl)-phenyl; 3'-(2-furyl)-phenyl, 3'-(2-oxazolyl)-phenyl, 3'-(3-isoxazolyl)-phenyl, 3'-(2-benzoxazolyl)-phenyl, 3'-(3-benzoisoxazolyl)-phenyl, 3'-(2-thiazolyl)-phenyl, 3'-(2-pyridyl)-phenyl, or 3'-(2-thienyl)-phenyl; or Ar is a heteroaryl ring selected from pyridine, pyrrole, thiophene, furan, or indole.

2. A compound according to claim 1 selected from:
4-{(1R)-1-[(phenylsulfonyl)amino]ethyl}phenyl trifluoromethanesulfonate;
N-[(1R)-1-(3-benzoylphenyl)ethyl]benzenesulfonamide;
4-{(1R)-1-[(pyridine-3-ylsulfonyl)amino]ethyl}phenyl trifluoromethanesulfonate;
N-[(1R)-1-(3-benzoylphenyl)ethyl]methanesulfonamide;
N-[(1R)-1-[3-(2-furoyl)phenyl]ethyl}thiophene-2-sulfonamide;
N-[(1R)-1-[3-(2-furoyl)phenyl] ethyl}methanesulfonamide;
4-{(1R)-1-[(thien-2-ylsulfonyl)amino]ethyl}phenyl trifluoromethanesulfonate;
N-[(1R)-1-(3-benzoylphenyl]ethyl}thiophene-2-sulfonamide;
N-[(1R)-1-(3-benzoylphenyl]ethyl}-3-pyrrolidin-1-ylpropane-1-sulfonamide;
methyl 5-({[(1R)-1-(3-benzoylphenyl)ethyl] amino}sulfonyl)-2-furoate;
5-({[(1R)-1-(3-benzoylphenyl)ethyl]amino}sulfonyl)-2-furoic acid;
4-{(1R)-2-methyl-1-[(methylsulfonyl)amino] propyl}phenyl trifluoromethanesulfonate;
N-((1R)-1-{4-[1-methyl-1-(phenylsulfonyl)ethyl] phenyl}ethyl)methanesulfonamide;
4-[(1R)-1-(isobutyrylamino)ethyl]phenyl trifluoromethanesulfonate;
4-{[(1R)-1-(pyridine-3-ylcarbonyl)amino]ethyl]}phenyl trifluoromethanesulfonate;
N-[(1R)-1-(3-benzoylphenyl)ethyl]benzamide;
N-[(1R)-1-(3-benzoylphenyl)ethyl]-2-furamide;
N-[(1R)-1-(3-benzoylphenyl)ethyl]cyclobutanecarboxamide;
N-[(1R)-1-(4-trifluoromethanesulfonyloxy)phenylethyl]-4-piperidin-1-ylbutanamide;
4-{(1R)-1-[(4-pyrrolidin-1-ylbutanoyl)amino]ethyl]}phenyl trifluoromethanesulfonate; or
(3-{(1R)-1-[(4-trifluoromethyl-1,3-thiazol-2-yl)amino] ethyl]}phenyl) (phenyl)methanone.

3. A method for treating a disease that involves C5a induced chemotaxis of human PMNs, selected from the group consisting of sepsis, psoriasis, bullous pemphigoid, rheumatoid arthritis, ulcerative colitis, acute respiratory distress syndrome, idiopathic fibrosis, cystic fibrosis, chronic obstructive pulmonary disease, glomerulonephritis injury caused by ischemia and reperfusion, comprising administering to a patient in need thereof an effective amount of a compound according to claim 1.

4. A method for treating sepsis, psoriasis, bullous pemphigoid, rheumatoid arthritis, ulcerative colitis, acute respiratory distress syndrome, idiopathic fibrosis, cystic fibrosis, chronic obstructive pulmonary disease, glomerulonephritis or injury caused by ischemia and reperfusion, comprising administering to a patient in need thereof an effective amount of a compound according to claim 1.

5. A method for the preparation of (R)-arylalkylamines of formula (IV)

wherein Ar and R1 are as defined in claim 1, comprising the steps of transforming the corresponding arylalkyl carboxylic acid into the corresponding acid azide, rearranging said azide into the corresponding isocyanate by Curtius reaction, and converting the isocyanate into an amine by acidic hydrolysis to produce the compound of formula (IV).

6. A method for the preparation of a compound of formula (I)

wherein R is CORa, SORa or $SO_2R_3$, and Ra is as defined in claim 1, comprising reacting an (R)-arylalkylamine of formula (IV)

wherein Ar and $R_1$ are as defined in claim 1, with a corresponding acyl, sulfinyl or sulfonyl chloride to produce the compound of formula (I).

7. A pharmaceutical composition comprising a compound according to claim 1 in admixture with a suitable carrier thereof.

8. A compound according to claim 1, wherein:
R is:
  2-thiazolyl, unsubstituted or substituted by a methyl or trifluoromethyl group; or
  CORa, $SO_2Ra$, or SORa;
wherein
Ra is selected from:
  $C_1$-$C_5$-alkyl, or $C_3$-$C_5$-cycloalkyl;
  phenyl, 3-pyridyl, 2-thiazolyl, 2-furyl, 5-(2-furoylmethyl), 5-(2-furoyl), 2-pyrrolyl, 2-thienyl, or 2-indolyl;
  a carboxylalkyl group of straight or branched $C_1C_6$-alkyl, or $C_1$-$C_6$-phenylalkyl;
or
  an ω-alkylamino group of formula II,
wherein X is linear or branched $C_1$-$C_6$ alkylene, $C_4$-$C_6$ alkenylene, or $C_4$-$C_6$ alkynylene; or X together with the nitrogen atom to which it is bound and with the $R_2$ group forms a nitrogen containing 3-7 membered heterocyclic monocyclic ring; and $R_3$ is hydrogen or $C_1$-$C_4$ alkyl;
$R_2$ and $R_3$ are independently hydrogen, linear or branched $C_1$-$C_6$ alkyl, $C_3$-$C_7$ cycloalkyl, $C_3$-$C_6$ alkenyl, or $C_3$-$C_6$-alkynyl;

or $R_2$ and $R_3$ together with the N atom to which they are bound, form a 4-6 membered nitrogen containing heterocyclic ring of formula (III), wherein Y represents $CH_2$, O, S, or an N—$R_6$ group, where $R_6$ is hydrogen, $C_1$-$C_4$ alkyl, or $C_1$-$C_4$ acyl, and p represents an integer from 0 to 2;

$R_1$ is methyl; and

Ar is 3'-benzoylphenyl, 4'-trifluoromethanesulfonyloxyphenyl, 3'-(furan-2-carbonyl)-phenyl, or 3'-(benzofuran-2-carbonyl)-phenyl.

* * * * *

UNITED STATES PATENT AND TRADEMARK OFFICE
CERTIFICATE OF CORRECTION

PATENT NO.        : 8,026,367 B2
APPLICATION NO.   : 12/094837
DATED             : September 27, 2011
INVENTOR(S)       : Allegretti et al.

Page 1 of 1

It is certified that error appears in the above-identified patent and that said Letters Patent is hereby corrected as shown below:

On the Title page, Item (56), under OTHER PUBLICATIONS, insert --Ranogajec et al.-- reference on a new line.

Column 7, Line 18, replace "Carréet al." with --Carré et al.--.

Column 8, Line 60, replace "+350" with --+35°--.

Column 9, Line 2, replace "+48.50" with --48.5°--;

Line 8, replace "+270" with --+27°--;

Line 13, replace "+45.50" with --+45.5°--;

Line 19, replace "+720" with --72°--.

Column 10, Lines 11-12, replace "10.40 (bs, 1H, $NH^+$)" with --10.40 (bs, 1H, $NH^-$)--.

Column 11, Lines 33-34, replace "(2R)-3-methyl-2-[4(trifluoromethylsllfonyloxy)phenyl]butanoic acid"
    with --(2R)-3-methyl-2-[4(trifluoromethylsulfonyloxy)phenyl]butanoic acid--.

Column 13, Line 38, replace "+180" with --+18°--.

Signed and Sealed this
Twenty-eighth Day of August, 2012

David J. Kappos
*Director of the United States Patent and Trademark Office*